United States Patent [19]

Sramek

[11] Patent Number: 4,874,604

[45] Date of Patent: Oct. 17, 1989

[54] HAIRSPRAY WITH IMPROVED ADHESION/REMOVABILITY UPON WASHING

[75] Inventor: John A. Sramek, Racine, Wis.

[73] Assignee: S. C. Johnson & Son, Inc., Racine, Wis.

[21] Appl. No.: 213,566

[22] Filed: Jun. 23, 1988

[51] Int. Cl.$^4$ .............................................. A61L 7/11
[52] U.S. Cl. ......................................... 424/47; 424/71
[58] Field of Search ..................................... 424/47, 71

[56] References Cited

U.S. PATENT DOCUMENTS

| | | | |
|---|---|---|---|
| 2,305,356 | 12/1942 | Luckenbach | 424/47 |
| 2,996,471 | 8/1961 | Reiter et al. | 260/334 R |
| 3,025,219 | 3/1962 | Maeder | 424/70 |
| 3,026,250 | 3/1962 | Coyner | 424/47 |
| 3,069,390 | 12/1962 | Kline | 424/47 |
| 3,178,353 | 4/1965 | Scheller et al. | 167/87 |
| 3,257,281 | 6/1966 | Maeder | 167/87.1 |
| 3,262,917 | 7/1966 | Maeder | 260/78.5 |
| 3,330,731 | 7/1967 | Mehaffey | 167/87 |
| 3,405,084 | 10/1968 | Bohac et al. | 424/47 |
| 3,427,382 | 2/1969 | Haefele | 424/47 |
| 3,485,915 | 12/1969 | Gerstein et al. | 404/87 |
| 3,577,517 | 5/1971 | Kubot et al. | 424/47 |
| 3,577,518 | 5/1971 | Shepherd et al. | 424/47 |
| 3,634,368 | 1/1972 | Palmer | 424/47 |
| 3,692,893 | 9/1972 | Palmer | 424/47 |
| 3,723,616 | 3/1973 | Erlemann et al. | 424/47 |
| 3,726,288 | 4/1980 | Nowak et al. | 424/47 |
| 3,728,319 | 4/1973 | Kiesel et al. | 260/88.1 |
| 3,735,003 | 5/1973 | Zimmer et al. | 424/47 |
| 3,799,933 | 3/1974 | Flown et al. | 424/47 |
| 3,800,033 | 3/1974 | Flawn et al. | 424/47 |
| 3,810,977 | 5/1974 | Levine et al. | 424/47 |
| 3,850,178 | 11/1974 | Schoenholz | 424/47 |
| 3,862,306 | 1/1975 | Block et al. | 424/47 |
| 3 876,760 | 4/1975 | Nersesian et al. | 424/70 |
| 3,907,984 | 3/1975 | Calvert et al. | 424/47 |
| 3,927,199 | 12/1975 | Micchelli et al. | 424/47 |
| 3,974,128 | 8/1976 | Block et al. | 424/47 |
| 3,981,987 | 9/1976 | Linke et al. | 424/47 |
| 4,036,241 | 7/1977 | Karg et al. | 424/47 |
| 4,044,121 | 11/1977 | Rosenberg et al. | 424/47 |
| 4,048,192 | 9/1977 | Stoll et al. | 260/334 R |
| 4,059,688 | 11/1977 | Rosenberg et al. | |
| 4,070,320 | 1/1978 | Meyer-Stoll et al. | 424/47 |
| 4,133,865 | 5/1964 | Richardson et al. | 424/47 |
| 4,134,968 | 2/1979 | Stebles | 424/47 |
| 4,164,562 | 8/1979 | Nandaqiri et al. | 424/47 |
| 4,192,861 | 3/1980 | Micchelli et al. | 424/47 |
| 4,196,190 | 4/1980 | Gehman et al. | 424/47 |
| 4,240,450 | 12/1980 | Grollier et al. | 424/47 |
| 4,263,275 | 4/1981 | Nandagiri | 424/47 |
| 4,275,055 | 6/1981 | Nachtigal et al. | 424/70 |
| 4,315,910 | 2/1982 | Nowak et al. | 424/47 |
| 4,324,780 | 4/1982 | Jacquet et al. | 424/47 |
| 4,409,379 | 11/1983 | Gaetani et al. | 424/47 |
| 4,450,091 | 5/1984 | Schmolka | 424/70 |
| 4,526,781 | 7/1985 | Goldberg et al. | 424/47 |
| 4,567,040 | 1/1986 | Varco et al. | 424/47 |
| 4,597,895 | 7/1986 | Bartlett | 424/47 |
| 4,614,200 | 9/1986 | Hsiung et al. | 424/70 |
| 4,689,379 | 8/1987 | Chuang | 424/47 |
| 4,726,945 | 2/1988 | Patel et al. | 424/70 |

FOREIGN PATENT DOCUMENTS

| | | | |
|---|---|---|---|
| 0239084 | 9/1987 | European Pat. Off. | |
| 7110434 | 7/1967 | Japan | 424/47 |
| 1321836 | of 0000 | United Kingdom | |
| 1243470 | 1/1969 | United Kingdom | 424/47 |

OTHER PUBLICATIONS

Service Bulletin GC-36 Revised, "Carbopol Water-soluble resins", B. F. Goodrich Chemical Division, Cleveland Ohio 65 pp.

Scafidi et al., "Use of fatty acid amido alkyldimethylamines in lotions", Reprint from Cosmetics and Perfumery for Apr. 1974, 3 pp.

National Starch & Chemical Corp. Specality Chemicals Bulletin "Technical Information: Amphomer ®" (12182 Superceded 12280) 8 pages, 1980, see p. 6 and 7.

Primary Examiner—Ellis P. Robinson
Assistant Examiner—P. L. Prater

[57] ABSTRACT

That which is disclosed is carboxyl radical containing resin hair setting or hair spray compositions possessing improved adhesion to the hair and which are more readily removed from the hair due to the use of certain long chain amine functional neutralizing agents containing a hydrophilic radical in addition to the amine radical as well as a long chain hydrocarbon radical such as lauryamidopropyl dimethylamine, polyoxyethylene (10) octadecylamine or a mixture of ether amines of the formula $R^6O(CH_2)_3NH_2$ where R is a hydrocarbon radical predominantly composed of $C_{12}$ to $C_{15}$ hydrocarbon radicals. Up to 40%, and preferably from 5% to 30%, of the moles of carboxyl radicals to be neutralized are neutralized with such a long chain amine and the remainder of the carboxyl radicals to be neutralized are neutralized with an amine or an alkanolamine such as aminomethyl propanol. More preferably, the compositions are hairspray compositions containing from about 10 to 80% by weight of a hydrocarbon-based aerosol propellant such an n-butane or isobutane. The long chain amine serves to improve the hydrocarbon stability of such hairspray resins.

23 Claims, No Drawings

HAIRSPRAY WITH IMPROVED ADHESION/REMOVABILITY UPON WASHING

BACKGROUND OF THE INVENTION

1. Field of the Invention

This invention relates to carboxyl radical containing resin hair setting or hairspray compositions possessing improved adhesion to the hair which are more readily removed from the hair due to the use of certain long chain amine-functional neutralizing agents containing a hydrophilic radical in addition to the amine radical as well as a long chain hydrocarbon radical. Such neutralizing agents also improve the compatibility of hairspray resins with hydrocarbon propellants.

2. Description of the Prior Art

Hair setting and hairspray resins are generally based on the use of polymers which are inherently water soluble such as those based on polyvinylpyrrolidone and those which are generally hydrophobic, but are rendered water soluble by virtue of the presence of pendant groups such as carboxyl radicals.

In the latter case, the polymers are rendered water soluble of water dispersible by neutralizing the carboxyl radicals to form a water soluble ammonium complex (e.g., using ammonium hydroxide) or an amine complex (e.g., using 2-amino-2-methyl-1-propanol also known as "aminomethyl propanol"). Examples of neutralizing agents are given in U.S. Pat. Nos. 2,996,471 to Reiter et al. and 4,192,861 to Micchelli et al. The number of such pendant radicals and the percentage of the same which are neutralized determines the solubility in water and hydrophilic solvents such as ethanol which are commonly used as solvents in hairsprays for reasons of non-toxicity and lack of disagreeable odor.

The degree of neutralization is generally balanced against the reduction of hydrophilicity caused by such neutralization. The remainder of the polymer is typically hydrophobic to provide desired dry film characteristics and also compatibility with solvents and any aerosol propellants that may be used to deliver the hairspray resin to the hair. Too much neutralization may result in moisture sensitive films which tend to become tacky and may result in separation of the polymer from the solvent and/or propellant in the container due to loss of the hydrophobic character of the resin that provides hydrocarbon compatibility. Some hairspray resins such as those based on acrylic acid or methacryclic acid as the source of carboxyl radicals along with more hydrophobic alkyl acrylates and/or alkyl methacrylates are not as soluble as formulators desire in the hydrocarbon propellants now favored over fluorocarbon propellants for ecological reasons.

U.S. Pat. No. 4,192,861 to Micchelli et al. addresses the problem of reduced hydrocarbon compatibility in neutralized hairspray resins derived from copolymers of unsaturated monocarboxylic acids and vinyl or vinylidene monomers by neutralizing at least 50% of the carboxyl radicals desired to be neutralized with specific long chain amines. The amines taught as being useful for this purpose are primary, secondary or tertiary long chain amines wherein the long chain amines contain 8 to 20 carbon atoms and preferably 12-18 carbon atoms such as actadecyl amine, octyl amine, hexadecyl amine, and stearyl amine. None of the long chain amines taught contain any functional groups other than the amine radical. The minor remaining amount of the neutralizing agent can optionally be conventional amines used to neutralize hairspray resins such as aminomethyl propanol. This provides a simple method to increase the hydrocarbon compatibility of the hairspray resin. However, it can decrease the water solubility of the resin since the only functional group present is the amine group which complexes with the carboxyl radical of the resin leaving the hydrophobic tail portion of the amine extending away from the complex.

British Pat. No. 1,321,836 to Wilson has a disclosure similar to that of the Micchelli et al. Patent. It teaches improving the aerosol propellant (halogenated hydrocarbons are preferred) compatibility of hairspray resins based on unsaturated dicarboxylic acids such as maleic acid and a vinyl or vinylidene monomer which have been partially esterified by reacting from 5-20% of the remaining carboxyl groups with a primary amine containing from 4 to 16 carbon atoms. The only amines taught contain a single hydrocarbon radical in addition to the $-NH_2$ radical. An additional number of carboxyl radicals can be neutralized with conventional neutralizing agents such as aminomethyl propanol.

U.S. Pat. No. 2,996,471 to Reiter et al. teaches improving the water solubility of a copolymer of vinyl acetate and crotonic acid for use in hairspray applications by reacting the carboxyl groups present with amino alcohols such as aminomethyl propanol or 2-amino-1-phenyl-1-butanol.

Another example of a method by which the characteristics of resins based on N-vinylpyrrolidone monomer can be modified is found in U.S. Pat. No. 3,728,319 to Kiesel et al. It teaches reacting a preformed polymer of N-vinylpyrrolidone or copolymers of that monomer with other unsaturated monomers with secondary or tertiary amines having alkyl groups of 1 to 50 carbons to produce an amino-alkylated polymer that is useful as an electrostatic toner dispersant or intermediate for making quaternized polymers or polymers containing amine oxide radicals. The amine must be reacted with the N-vinylpyrrolidone radicals in the polymer using a free radical catalyst.

On pages 6 and 7, National Starch and Chemical Corporation Specialty Chemicals Bulletin "Technical Information: *AMPHOMER* ®" (12182 Supercedes 12280) teaches the use of MONAMID 716 (Lauramide DEA) from Mona Industries in various hairsprays containing AMPHOMER resin which is a carboxylated acrylic hairspray resin that is further described infra. However, the MONAMID 716 appears to be added as a hair conditioner since the amide radical in the Lauramide DEA (diethanolamide) does not function as a neutralizing agent.

SUMMARY OF THE INVENTION

The present invention provides a hair setting, and, more preferably, a hairspray composition—in the form of a pump spray or a self-pressurized aerosol composition—employing a carboxyl radical-functional hair setting or hairspray resin which possesses improved adhesion to the hair because a minor portion of the total carboxyl radicals neutralized are neutralized with a specific type of long chain amine. That amine contains both a long chain aliphatic hydrocarbon radical and a hydrophilic radical which provides a degree of water solubility to the long chain amine after complexation with carboxyl radicals present in the resin.

Another advantage of the present invention is that the presence of the hydrophilic radical tends to increase the ability of the hairspray resin to be removed from the hair by washing or shampooing even though the long chain amine contains a hydrophobic long chain aliphatic hydrocarbon radical. Improved water solubility also enables hairspray compositions to be placed on damp hair with good results unlike less water soluble compositions which tend to flake off upon drying if placed on damp or wet hair due to their more hydrophobic nature.

Still another advantage of the present invention is that the presence of the hydrophobic long chain aliphatic hydrocarbon radical provides improved compatibility with hydrocarbon propellants when a hairspray resin is neutralized according to the present invention.

These and other advantages of the present invention are provided by a hair setting composition comprising from about 0.5% to 8% by weight of a hair setting resin containing pendant carboxyl radicals such as an acrylic addition polymer formed from methacrylic acid and other unsaturated monomers such as alkyl acrylates and alkyl methacrylates and a solvent for the resin wherein from about 10% to 100% of the carboxyl radicals are neutralized with a neutralizing agent consisting of (a) up to 40 mole percent, based on the mole percent of carboxyl radicals to be neutralized, of a long chain amine selected from the group consisting of amidoamines having a long chain hydrocarbon radical such as lauramidopropyl dimethylmaine, PEG-10 stearamine and a mixture of ether amines of the formula $R^6O(CH_2)_3NH_2$ where $R^6$ is a hydrocarbon radical predominantly composed of $C_{12}$ to $C_{15}$ hydrocarbon radicals and (b) the balance of the neutralizing agent being an amine or alkanolamine such as aminomethyl propanol. More preferably, the amount of long chain amine is in the range of from about 5% to about 30% of the total percentage of carboxyl groups neutralized in the resin.

More preferably, the hairspray composition is one wherein from about 10% to about 80%, and more preferably from 20% to 50%, based on the total weight of the composition, of a hydrocarbon-based aerosol propellant such as n-butane or isobutane is employed to obtain a self-dispensing aerosol hairspray composition. In such propellant-containing formulations, the amount of hairspray resin is preferably from about 0.5% to 6% of the total weight of the composition.

DETAILED DESCRIPTION OF THE PRESENT INVENTION

This inventions relates to a hair setting composition having improved adhesion to the hair and removability from the hair upon washing comprising from 0.5% to 8% by weight of a hair setting resin containing pendant carboxyl radicals and a solvent for the resin wherein from about 10% to 100% of the carboxyl radicals are neutralized with a neutralizing agent consisting of (a) up to 40 mole percent, based on the mole percent of the carboxyl radicals to be neutralized, of at least one long chain amine selected from the group consisting of $$R^1CONHR^2NR^3R^4$$

where $R^1$ is a hydrocarbon radical having from about 9 to 14 carbon atoms, $R^2$ is an alkylene radical of 2 to 4 carbon atoms, and each of $R^3$ and $R^4$ are alkyl radicals of 1 to 2 carbon atoms or hydrogen.

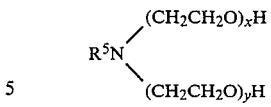

where $R^5$ is a hydrocarbon radical having from 10 to 18 carbon atoms and the sum of $X+y$ has an average value of from about 5 to 25, and

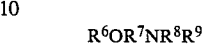

where $R^6$ is a hydrocarbon radical of from 8 to 16 carbon atoms, $R^7$ is an alkyl radical of 1 to 2 carbon atoms, and each of $R^8$ and $R^9$ are alkyl radicals of 1 to 2 carbon atoms of hydrogen; and (b) the balance of the neutralizing agent being a water soluble, cosmetically acceptable basic compound.

In a more preferred embodiment, this invention further relates to a hairspray composition which, in addition to the above ingredients, further contains from about 10% to about 80%, more preferably between 20% and 50% of a volatile hydrocarbon propellant of the type commonly used in hairspray compositions which can include liquified lower hydrocarbons of 3 to 4 carbon atoms such as propane, n-butane, and isobutane.

Any conventional resin-containing pendant carboxyl radicals known to be suitable for holding the hair in a desired style can be employed. Resins which are too high in viscosity and molecular weight to be sprayed from an aerosol container can be applied to the hair in lotion, gel or other conventional form. Thus, "hair setting resins" as used herein includes "hairspray resins" which typically are sprayed from a pump spray or pressurized aerosol container. The resins useful in the present invention are typically referred to anionic polymers because of the presence of the carboxyl radicals. The resins are used in the compositions of the present invention in amounts between 0.5% to 8% of the total composition based on the nonvolatile solids content of the resin, and for use in aerosol propellant-containing compositions, 0.5% to 6% is more preferred.

Examples of anionic hair setting polymers are copolymers of vinyl acetate and crotonic acid; terpolymers of vinyl acetate, crotonic acid and a vinyl ester of an alpha-branched saturated aliphatic monocarboxylic acid such as vinyl neodecanoate; and copolymer of methyl vinyl ether and maleic anhydride (molar ratio about 1:1) wherein such copolymers are 50% esterified with a saturated aliphatic alcohol containing from 1 to 4 carbon atoms such as ethanol or butanol.

Another class of hair setting resins which are useful in the present invention are acrylic polymers containing acrylic acid or methacrylic acid as the carboxyl radical containing moiety and other esters of acrylic or methacrylic acid with $C_1$ to $C_{18}$ alcohols, hydroxymonoesters of acrylic acid or methacrylic acid with $C_2$ to $C_6$ glycols, hydroxymonoesters of acrylic acid or methacrylic acid with polyalkyleneoxy polymers containing up to about 25 units derived from ethylene oxide, propylene oxide and mixtures thereof, acrylamide, methacrylamide, and N-subsitituted acrylamides or methacrylamides substituted with alkyl radicals having from 2 to 12 carbon atoms. Acrylic polymers tend to have less hydrocarbon compatibility than other classes of hairspray polymers and are therefore preferred for use in the present invention. Examples of comonomers which can be employed with acrylic acid or methacrlyic acid are methyl methacrylate, ethyl methacrylate, butyl methacrylate, hexyl methacrylate, cyclohexyl methacrylate, octyl methacrylate, dodecyl methacrylate, methyl acrylate, ethyl acrylate, butyl acrylate, amyl acrylate, cyclohexyl acrylate, benzyl acrylate, octyl acrylate, octadecyl acrylate, acrylamide, methacrylamide, N-ethyl acrylamide, N-tertiary-butyl acrylamide, N-n-octyl acrylamide, N-tertiary-octyl acrylamide, N-decyl acrylamide and N-dodecyl acrylamide as well as the corresponding methacrylamides such as N-tertiary-octy methacrylamide and N-decyl methacrylamide, 2-hydroxypropyl acrylate, 2-hydroxypropyl methacrylate, 2-hydroxyethyl acrylate, 2-hydroxyethyl methacrylate, $HO(CH_2CH_2O)_a(C_bH_{2b})OOCC(CH_3)=CH_2$ where a is 5 to 20 and b is 1 to 4. One example of a presently preferred acrylic polymer which can be employed in the compositions of the present invention is a polymer of tertiary-butyl acrylamide, acrylic acid and ethyl acrylate which is commercially sold by BASF Corporation under the name BASF ULTRAHOLD 8 (CTFA (Cosmetic, Toiletry and Fragrance Association) designation: Acrylate/Acrylamide Copolymer). Another example of a presently preferred acrylic polymer is a terpolymer of methacrylic acid, butyl acrylate and ethyl methacrylate.

Such anionic hair setting and hairspray polymers are known in the art as can be seen from an examination of U.S. Pat. Nos. 3,405,084 to Bohac et al.; 3,577,517 to Kubot et al.; 3,577,518 to Shepard et al.; 3,927,199 to Micchelli; 4,192,861 to Micchelli et al.; 4,192,862 to Pengilly et al.; and 4,240,450 to Grollier et al. which are hereby incorporated by reference to teach such polymers.

Amphoteric polymers which contain cationic radicals derived from monomers such as t-butyl aminoethyl methacrylate as well as carboxyl radicals derived from monomers such as acrylic acid or methacrylic acid can also be used in the compositions of the present invention. One example of a presently preferred amphoteric polymer which can be used in the present invention is a polymer sold under the trademark AMPHOMER by National Starch and Chemical Corporation which has the CTFA name of Octylacrylamide/Acrylates/-Butylaminoethyl Methacrylate Copolymer and is described in U.S. Pat. No. 4,192,861 as being a polymer of N-tert-octyl acrylamide, methyl methacrylate, hydroxypropyl methacrylate, acrylic acid and t-butyl aminoethyl methacrylate. Examples of such polymers are found in U.S. Pat. No. 3,726,288 to Nowak et al.; 3,981,987 to Linke et al.; 4,237,253 to Jacquet et al. and 4,358,567 to Hayama et al. which are hereby incorporated by reference to teach such polymers.

Generally, a large number of commercially available anionic and amphoteric hair setting and hair spray resins derive their carboxyl radical functionality from one of the following monomers: acrylic acid, methacrylic acid, crotonic acid and maleic anhydride.

The resins are dissolved in a conventional non-toxic solvent or solvent system of the type commonly used in hair setting and hairspray compositions such as $C_2$ to $C_4$ alcohols such as ethanol, isopropanol and tertiary-butanol, with ethanol and isopropanol being preferred for hairspray compositions. Hairspray compositions may also contain water as a solvent although it is generally advisable to use the minimum amount of water needed since water tends to release the curls in the hair. For hairsprays, generally less than 10% of the total composition, exclusive of propellant, is water. Compositions of the present invention may also contain small amounts of other types of solvents such as methoxyethanol and 2-ethoxyethanol which do not provide the composition with an odor.

On the other hand, for lotion or gel hair setting compositions, a substantial amount of the solvent can be water with only a minor amount of the solvent present being a cosolvent such as ethanol, ethylene glycol or a glycol ether such as 2-ethoxyethanol. Lotion or gel formulations may be thickened using less than about 5% and typically about 1-2% by weight of conventional thickening agents such as water soluble cellulosics such as hydroxyethyl cellulose or hydroxypropyl cellulose or one of the acrylic acid homopolymers crosslinked with a small amount of a polyallyl ether of sucrose sold under the tradenames CARBOPOL 940 AND 941 by B. F. Goodrich Chemical Company, the latter of which are typically neutralized before use with an alkaline material such as sodium hydroxide.

When the hair spray compositions are to be dispensed from a presurized aerosol container, a propellant which may consist of one or more aerosol type propellant compounds may be used to propel the compositions out of the container onto the hair. These propellants are well known to those skilled in the art and are commercially available. Examples of such propellants can be liquified lower hydrocarbons such as propane, n-butane, and isobutane and the low boiling chlorofluorohydrocarbons such as trichlorofluoromethane, dichlorofluoromethane and 1,2-dichloro-1,1,2,2-tetrafluoroethane and mixtures thereof. Other examples of propellants are dimethyl ether, nitrogen and carbon dioxide.

In accordance with procedures which are well known in the art, all propellants are used in sufficient quantities to provide a pressurizing amount of such propellants within the aerosol spray container to be used. Generally, propellants are employed as from 10 to 80 percent by weight of the hair spray composition and more preferably between 20 and 50 percent by weight of the total composition. As noted earlier, the present invention is of particular advantage when hydrocarbon propellants are employed because the long chain amines which will now be described in further detail provide improved hydrocarbon compatibility over resins simply neutralized with conventional neutralizing agents such as aminomethyl propanol.

Long chain amines useful as neutralizing agents in the present invention are primary, secondary and tertiary amines which further contain a long chain hydrocarbon radical as well as a hydrophilic group removed from the amine nitrogen atom to retain hydrophilic characteristics to the amine/carboxyl radical complex formed upon neutralization of the carboxyl radical by the long chain amine. The hydrophilic group contributes to the removability of the hair setting resin from the hair upon washing or shampooing by retaining the water solubility or dispersibility of the polymer in spite of the presence of the long chain hydrocarbon group. At the same time, it improves the adhesion of the hair fibers to each other after the hair is treated with compositions of the present invention. The long chain hydrocarbon radical has a sufficient number of carbon atoms to provide improved hydrocarbon propellant compatibility.

Examples of such long chain amines are amido amines of the general formula $R^1CONHR^2NR^3R^4$ where $R^1$ is a hydrocarbon radical having from 9 to 14 carbon atoms, $R^2$ is an alkylene radical or 2 to 4 carbon atoms, and each of $R^3$ and $R^4$ are alkyl radicals of 1 to 2 carbon atoms of hydrogen. Examples of such amido amines (CTFA designated names are given parenthetically) are N-[3-(dimethylamino)propyl]coco amides ("coamidopropyl dimethylamine"); N-[3-(dimethylamino)propyl]pentadecanamide; N-[3-(dimethylamino)propyl]dodecanamide ("lauramidopropyl dimethylamine"); and N-[2-(diethylamino)ethyl]-dodecaneamide. Preferably, $R^1$ contains 11 carbon atoms and lauramidopropyl dimethylamine is preferred as the long chain amine compound. As is well known, commercially available amines of this and the following types are typically composed of mixtures of amines having different hydrocarbon groups such as the coco amides where the long chain amines are derived from coconut fatty acids. A number of these long chain amines are available commercially under the tradename of LEXAMINE ® from Inolex Chemical Company of Chicago, Illinois.

Other long chain amines can be N-ethoxylated amines of the formula $$R^5N \begin{matrix} (CH_2CH_2O)_xH \\ (CH_2CH_2O)_yH \end{matrix}$$

where $R^5$ is a hydrocarbon radical having from 10 to 18 carbon atoms and the sum of $x+y$ has an average value of from about 5 to 25. Examples of such N-ethoxylated amines are:
polyoxyethylene (5) cocoamine ("PEG-5 cocamine");
polyoxyethylene (10) cocoamine ("PEG-10 cocamine");
polyoxyethylene (15) cocoamine ("PEG-15 cocamine");
polyoxyethylene (25) cocoamine;
polyoxyethylene (5) octadecylamine ("PEG-5 stearamine");
polyoxyethyl (10) octadecylamine ("PEG-10 stearamine");
polyoxyethyl (15) octadecylamine ("PEG-15 stearamine");
polyoxyethyl (20) octadecylamine;
polyoxyethyl (25) octadecylamine;
polyoxyethyl (5) tallowamine ("PEG-5 tallow amine");
polyoxyethyl (15) tallowamine ("PEG-15 tallow amine");
polyoxyethyl (5) oleylamine ("PEG-5 oleamine");
polyoxyethyl (15) oleylamine ("PEG-15 oleamine");
polyoxyethyl (5) soyaamine ("PEG-5 soyamine");
polyoxyethyl (10) soyaamine ("PEG-10 soyamine");
polyoxyethyl (15) soyaamine ("PEG-15 soyamine"); and
polyoxyethyl (25) soyaamine. Preferably, the polyethoxylated amine is one of the above formula wherein R is 18 and $x+y$ has an average value of 10. A number of these long chain amines are available commercially under the tradename of ETHOMEEN ® from Akzo Chemie America, Armak Chemicals of Chicago, Illinois. PEG-10 Stearamine is presently preferred.

Still another example of long chain amines useful in the present invention are long chain ether amines of the formula $R^6OR^7NR^8R^9$ where $R^6$ is a hydrocarbon radical of from 8 to 16 carbon atoms, $R^7$ is an alkyl radical of 1 to 2 carbon atoms, and each of $R^8$ and $R^9$ are alkyl radicals of 1 to 2 atoms of hydrogen. Examples of such amines are those sold under the tradename of ADOGEN ® Primary Ether Amines by Sherex Chemical Company, Inc. of Dublin, OH: $C_{10}H_{21}O(CH_2)_3NH_2$ where the $C_{10}H_{21}$-radical is branched which is sold as ADOGEn 180 Primary Ether Amine; $C_{13}H_{27}O(CH_2)_3NH_2$ where the $C_{13}H_{27}$-radical is branches which is sold as ADOGEN 183 Primary Ether Amine; $C_{14}H_{29}O(CH_2)_3NH_2$ which is sold as ADOGEN 184 Primary Ether Amine; $C_rH_{2r+1}O(CH_2)_3NH_2$ where substantially all of the r values are integers of 12 to 15 and about 1% of the r values are 10 and 16, respectively which is sold as ADOGEN 185 Primary Ether Amine; $C_rH_{2r+1}O(CH_2)_3NH_2$ where substantially all of the r values are integers of 8 to 10 and about 1% of the r values are 6 and 12, respectively which is sold as ADOGEN 188 Primary Ether Amine; $C_rH_{2r+1}O(CH_2)_3NHCH_3$ where substantially all of the r values are integers of 12 to 15; $C_rH_{2r+1}O(CH_2)_3N(CH_3)_2$ where substantially all of the r values are integers of 12 to 15; $C_{13}H_{27}O(CH_2)_3N(CH_3)CH_2CH_3$ where the $C_{13}H_{27}$-radical is branched; $C_{13}H_{27}O(CH_2)_3N(CH_2CH_3)_2$ where the $C_{13}H_{27}$- radical is branched; $C_rH_{2r+1}O(CH_2)_2NHCH_3$ where substantially all of the r values are integers of 12 to 15; $C_rH_{2r+1}O(CH_2)_2N(CH_3)_2$ where substantially all of the r values are integers of 12 to 15; and $C_{13}H_{27}O(CH_2)_2N(CH_3)CH_2CH_3$ where the $C_{13}H_{27}$-radical is branched; and $C_{13}H_{27}O(CH_2)_2N(CH_2CH_3)_2$ where the $C_{13}H_{27}$-radical is branched.

In formulating hair setting and hairspray compositions, it is preferably to use just enough long chain amine to obtain improved adhesion and removability from the hair as well as improved hydrocarbon compatibility in those formulations containing hydrocarbon propellants. Use of too much long chain amine can cause a reduction in adhesion values beyond a maximum obtained when an optimum level of amine is added. One first determines the degree to which the carboxyl radicals present in the polymer are to be neutralized in a conventional manner. Typically, about 10% to 100% of the stoichiometric amount of carboxyl radicals are neutralized. Polymers containing a significant percentage of carboxyl radicals, for example 20 weight percent of polymer or more, are typically neutralized to a lesser degree, e.g., 40% to 50% of the carboxyl radical content, than a polymer containing 10% or less carboxyl radical content where up to 100% of the carboxyl radicals are neutralized to provide the desired amount of water solubility or dispersibility. The degree of neutralization is also selected so that one minimizes obtaining a film which is so hydrophilic that the hair setting resin tends to become unacceptably tacky or sticky in humid environments.

After the desired level of neutralization is selected, up to 40% of the carboxyl radical to be neutralized are then neutralized with the above-described long chain amines. More preferably, from about 5% to 30% of the carboxyl radicals to be neutralized are neutralized with such long chain amines. Long chain amines which are solids at room temperature such as lauramidopropyl dimethylamine are preferred because amines which are liquid at room temperature tend to plasticize the resin film on the hair and can also impart some odor to the compositions. Such solid long chain amines can also be used at higher levels than the liquid long chain amines because they do not have as much of a plasticizing effect. Generally, neutralizing between 7% and 23% of the total carboxyl radicals being neutralized using lauramidopropyl demthylamine with 3 weight percent of an acrylic polymer (i.e., about 3% to 17% of lauramidopropyl dimethylamine based on the weight of the acrylic resin) was found to give good levels of improved adhesion as will be shown in the following examples. It is expected that undesirable plasticization effects of liquid long chain amines can be minimized by limiting the weight of liquid amine used in the composition to no more than about 20 weight percent based on the weight of the hair setting resin.

The balance of the carboxyl radicals to be neutralized are neutralized with a water soluble, cosmetically acceptable basic compound such as any conventional amine or alkanolamine known to be suitable for use in hair setting and hairspray compositions. Examples of such amines and alkanolamines are as follows: ammonia, ammonium hydroxide, monoethanolamine, diethanolamine, triethanolamine, monopropanolamine, dipropanolamine, tripropanolamine, morpholine, aminoethyl ethanolamine, aminomethyl propanol, 2-amino-2-methyl-1,3-propanediol ("aminomethyl propanediol"), 4-morpholineethano, ammonium salts of lysine or glycine and mixtures thereof. "Cosmetically acceptable" means a basic compound which can be used with products intended for contact with the human body and which do not deleteriously change the solubility of the resin being neutralized so as to cause it to precipitate out of solution. Aminomethyl propanol is presently preferred.

The neutralization step can be carried out in a conventional fashion. The neutralizing agents are dissolved in the solvent and the resin is then added and mixed until a homogeneous solution is obtained. Alternatively, the resin can be dissolved in the solvent if it is sufficiently soluble to be dispersed without neutralization and then the neutralizing agents can be added. Thereafter, any additional optional additives to modify the properties of the composition can be added such as perfumes; plasticizers such as glycols, phthalate esters and glycerine; silicones; emollients; lubricants and penetrants such as lanolin compounds; protein hydrolyzates and other protein derivatives; dyes, tints and other colorants; thickeners, anticorrosion agents, Panthenol, preservatives, detackifying agents, combing aids, antistatic agents, etc. The order of addition of such optional ingredients is generally not critical.

Hair spray formulations are preferably prepared by dissolving the desired amount of neutralizing agent in the solvent to be used followed by addition to the hairspray resin. After the hairspray resin is dissolved, any optional ingredients are added to the solution and the composition obtained is packaged in a pump spray container if a non-pressurized aerosol product is desired. Otherwise, the composition is charged into a suitable pressurizable container which is sealed and then charged with a suitable propellant according to conventional techniques such as by adding a liquified propellant to the contents of the container under pressure. It is preferable to have all of the components of the spray composition mixed and homogeneous prior to the addition of the propellants. Alternatively, pressurized aerosol spray containers can be used where the propellant is separated from contact with the hairspray composition such as a two compartment can of the type sold under the tradename SEPRO from American National Can Corporation.

The compositions of the present invention can also be used as hair setting compositions which are applied to the hair in lotion or gel form. In this case, the procedure for making non-pressurized aerosols is employed, but a thickener is further added to the composition to increase its viscosity to the desired level according to conventional procedures. The product is then packaged in a bottle, tube or jar to be applied directly to the hair which can either be curled or combed to style the hair as desired.

The resulting hair setting compositions exhibit improved holding power over compositions without such long chain amine neutralizing agents as well as being more easily removed from the hair by washing or shampooing. When hydrocarbon propelled compositions are employed, the compatibility of the hair spray resin is generally improved.

The following examples are provided to show various aspects of the present invention without departing from the scope and spirit of the invention. Unless otherwise indicated, such as in reference to percentages of carboxyl radicals being neutralized which are on a stoichiometric basis, all parts and percentages used in the Examples are by weight.

In the following Examples, several tests were used to evaluate the compositions and their effect on hair and they were done as follows:

Haze test: The solution clarity and thus, the solubility in deionized water, of the propellant-free hair setting compositions were evaluated in this test. All of the ingredients of the compositions to be tested, except for the propellant which was omitted, were mixed together until the solution was homogeneous. In the test designated "50/50", 50 parts of the composition to be tested were mixed with 50 parts of deionized water and stirred until the diluted composition was homogeneous. In the test designated "10/90", 10 parts of the composition to be tested were mixed with 90 parts of deionized water and stirred until homogeneous. Each diluted solution was visually observed for clarity through a test tube which was 17 mm in diameter.

Aerosol clarity: In this test, the room temperature clarity of the aerosol propellant-containing compositions was observed visually after the compositions were pressurized and sealed within a transparent glass aerosol container. Room temperature is about 21° to 22° centigrade. The solution clarity was observed visually and noted in the following examples.

Chilled Aerosol Clarity: Aerosol propellant-containing compositions in transparent glass containers were placed in a freezer at 0° F. (−17.8° C.). The next day the clarity of the solution was observed visually and any precipitate (denoting incompatibility with the propellant) found was noted.

Knot Adhesion test: In this test, the adhesion of individual strands of hair taken from the same hair swatch were measured. Individual strands of virgin hair were taken from the same swatch and a single loop knot was in each strand of hair by twisting the strand into a loop and passing one end of the strand through the loop and pulling the ends until a loop approximately 1.5 cm on diameter was formed. 0.075 microliters of the product to be tested was then placed on the junction of each loop, i.e., at the point where the strand of hair overlaps to form the knot. Each looped strand containing the composition to be tested was then allowed to dry in an environmental chamber at a relative humidity of 38% and a temperature of 22° to 23° C. and were left in the chamber for a minimum of 1 hour to "condition" the strands. After such conditioning, the loop on the opposite side of the knot junction was cut and each of the non-looped ends was placed on the holder clip of an Instron testing machine, Model No. 4201 from Instron Corporation. The holder clips on the crosshead of the Instron machine were spread apart at a constant rate of 60 millimeters per minute and the test was deemed finished when the junction of the knot was broken. The response to the break was measured in "grams at break". The sampling rate during the test was 20 data points per second - measured electronically. A series of 20 individual strands were done for each test and the average value of the "grams at break" was reported as the Knot Adhesion value.

The following materials were used in the Examples:
Absolute Ethanol was 200 proof SDA 40-2 ethanol.
Acrylic Polymer A was a terpolymer of 31% methacrylic acid, 42% butyl acrylate, and 27% ethyl methacrylate made by an aqueous emulsion polymerization process wherein the resulting resin had (via a gel permeation chromatographic technique) a number average molecular weight ("$M_n$") of 73,600, a weight average molecular weight ("$M_w$") of 183,000 and a sedimentation average molecular weight ("$M_z$") of 312,000 where $M_z$ is defined in U.S. Pat. No. 4,529,787 to Schmidt et al. and the product used was in the form of an aqueous emulsion at 40% nonvolatile solids content.

Acrylic Polymer B was an aqueous emulsion polymer of the same composition and nonvolatile solids content as Acrylic Polymer A, but the resin had a $M_n$ of 20,090, $M_w$ of 126,510 and $M_z$ of 276,330.

Acrylic Polymer C was an aqueous emulsion polymer of the same composition and nonvolatile solids content as Acrylic Polymer B, but was a higher molecular weight version of that resin that had a $M_n$ of 30,600, $M_w$ of 760,970 and $M_z$ of 1,929,230.

ADMA 2 was dimethyl lauramine from Ethyl Corporation, equivalent weight=213.
ADMA 4 was dimethyl myristamine from Ethyl Corporation, equiv. weight=241.
ADOGEN 185 Primary Ether Amine was a mixture of ether amines of the formula $C_rH_{2r+1}O(CH_2)_3NH_2$ where substantially all of the r values are integers of 12 to 15 and about 1% of the r values are 10 and 16, respectively, which is sold by AKZO Chemie America, ARMAK Chemicals, equiv. weight=280.

ADOGEN 342D was dimethyl stearamine from Sherex Chemical Co., equiv. weight=298.
AMP-95 was aminomethyl propanol (95%) from International Minerals & Chemicals Corp., equiv. weight=94.
DOW CORNING ® 345 was decamethylcyclopentasiloxane (75%) and octamethylcyclotetrasiloxane (cyclomethicone) from Dow Corning Corp. Dow Corning ® Q2-5220 was dimethicone copolyol from Dow Corning Corporation.
ETHOMEEN 18/20 was polyoxyethylene (10) octadecylamine from AKZO Chemie America, ARMAK Chemicals, equiv. weight=705.
Hydrocarbon propellant A was a mixture of 0.01% ethane, 15.90% propane, 35.57% iso-butane and 48.52% n-butane. LEXAMINE L-13 was lauramidopropyl dimethylamine from Inolex Chemical Co., equiv. weight=287.
LEXAMINE P-13 was palmitamidopropyl dimethylamine from Inolex Chemical Co., equiv. weight=344.
PVP K-90 Resin was a homopolymer of N-vinylpyrrolidone having a molecular weight of about 630,000 from GAF Corporation.
SILWET L-7602 was dimethicone copolyol from Union Carbide Corp.
VARONIC K-215LC was polyoxyethylene (15) cocoamine from Sherex Chemical Co., equiv. weight=887.
VARONIC T-215 was polyoxyethylene (15) tallowamine from Sherex Chemical Co., equiv. weight=925.

EXAMPLES 1-8

In this series of Examples, the water solubility of hair spray compositions was observed using various types of long chain amines along with a control sample which did not contain any long chain amine. The acrylic polymer used as the hair spray resin was Acrylic Polymer A. The following compositions were made up, substituting the amounts of long chain amine (none in Example 8) indicated below into the following formula:

| | |
|---|---|
| Acrylic Polymer A | 5.0 |
| Long Chain Amine (see Table below) | 0.2 |
| Aminomethyl Propanol | 0.2 |
| DOW CORNING Q2-5220 | 0.2 |
| Fragrance | 0.15 |
| Absolute Ethanol | 64.25 |
| Hydrocarbon Propellant A | 30.0 |
| | 100.00% |

The following amines were employed in the above composition and the results of the Haze Test are reported below. The pH of the 50/50 dilution in deionized water is also reported below.

| Ex. | Long Chain Amine | Haze Test[1] 50/50 | Haze Test[1] 10/90 | pH (50/50) | Percent Neutr.[2] | Total Neutr.[3] |
|---|---|---|---|---|---|---|
| 1 | ETHOMEEN 18/20 | C | NE | 7.35 | 11.8 | 33.5 |
| 2 | LEXAMINE L-13 | C | C | 7.46 | 24.7 | 39.2 |
| 3 | LEXAMINE P-13 | H | H | 7.25 | 21.4 | 37.6 |
| 4 | VARONIC K-215LC | C | C | 7.27 | 9.6 | 32.6 |
| 5 | VARONIC T-215 | C | C | 7.25 | 9.2 | 32.5 |
| 6 | ADMA 4 | SH | SH | 7.50 | 28.0 | 40.9 |
| 7 | ADOGEN 342D | H | H | 7.44 | 24.0 | 38.8 |

-continued

| Ex. | Long Chain Amine | Haze Test[1] 50/50 | 10/90 | pH (50/50) | Percent Neutr.[2] | Total Neutr.[3] |
|---|---|---|---|---|---|---|
| 8 | No additional amine | C | C | 7.29 | 0 | 29.5 |

[1]C = Clear SH = Slightly hazy H = Hazy NE = Not evaluated
[2]Percent (Stoichiometric) of total carboxyl radicals neutralized, Which were neutralized with long chain amine.
[3]Percent (Stoichiometric) of carboxyl radicals neutralized by all amines present.

Example 3 shows that the 16 carbon atom long chain hydrocarbon group is too long to render adequate water solubility to the resulting composition.

Examples 6 and 7 show that long chain dimethylamines without any further hydrophilic groups present degrade the water solubility of the hair spray composition.

Example 8 is also comparative in that it shows that the aminomethyl propanol neutralized composition is also water soluble at both dilutions.

For all of the compositions tested, the appearance of the composition before addition of the hydrocarbon propellant was clear; the Aerosol Clarity Test and the Chilled Aerosol Clarity Test resulted in clear solutions; and each aerosol spray composition was observed to be clear and free of tackiness when sprayed on a clean glass slide and allowed to air dry. Thus, the long chain amines used in Examples 1, 2, 4 and 5 did not affect the water solubility of the composition.

EXAMPLES 9–17

In this series of Examples, various amines were evaluated with a composition based on Acrylic Polymer A using 40% hydrocarbon propellant A whereas Examples 1–8 used 30% Hydrocarbon Propellant A. The formulation was as follows:

| | |
|---|---|
| Acrylic Polymer A | 5.0 |
| DOW CORNING ® Q2-5220 | 0.2 |
| AMP-95 | 0.2 |
| Long Chain Amine (see Table below) | 0.2 |
| Fragrance | 0.15 |
| Absolute Ethanol | 54.25 |
| Hydrocarbon Propellant A | 40.0 |
| | 100.00% |

The following amines were used in the above described amount to prepare compositions which were then checked for compatibility with the Hydrocarbon Propellant A using the Aerosol Clarity and the Chilled Aerosol Clarity tests. The results were as follows:

| Ex. | Long Chain Amine | Aerosol Clarity[1] | Chilled Aerosol Clarity[1] | Percent Neutr.[2] | Total Neutr.[3] |
|---|---|---|---|---|---|
| 9 | LEXAMINE L-13 | C | C, No PPT | 24.7 | 39.2 |
| 10 | LEXAMINE P-13 | SH | No PPT | 21.4 | 37.6 |
| 11 | VARONIC K-215LC | CL | PPT | 9.6 | 32.6 |
| 12 | VARONIC T-215 | CL | PPT | 9.2 | 32.5 |
| 13 | ADMA 4 | SH | No PPT | 28.0 | 40.9 |
| 14 | ADOGEN 342D | SH | No PPT | 24.0 | 38.8 |
| 15 | No additional amine[4] | CL | PPT | 0 | 29.5 |
| 16 | ETHOMEEN 18/20 | CL | PPT | 11.8 | 33.5 |
| 17 | AMP-95 | CL, PPT | PPT | 0 | 59.0 |

[1]C = Clear SH = Slight haze CL = Cloudy PPT = Precipitate Present
[2]Percent of total carboxyl radicals neutralized, which were neutralized with long chain amine
[3]Percent of carboxyl radicals neutralized by all amine present.
[4]0.2% Absolute Ethanol was added.

Prior to addition of the Hydrocarbon Propellant A, all compositions were observed to be clear and free of visual haze. In this series, Example 9 gave the best results while Examples 15 and 17 which employed no long chain amines gave very poor results. At the level employed, ETHOMEEN 18/20 in Example 16 resulted in a cloudy solution with a precipitate: too little was employed. Comparative Examples 13 and 14 show that long chain amines did improve the hydrocarbon compatibility. Similarly, in Examples 11 and 12, the level of long chain amines was too low. Example 10 gave only a slight haze and no precipitate. Thus, the preferred long chain amine, LEXAMINE L-13, gave excellent results even at the low level of amine employed.

EXAMPLES 18–22

The following examples show the effect on adhesion resulting from the addition of LEXAMINE L-13, an inventive composition, and ADMA 2, a comparative composition of the type used in U.S. Pat. No. 4,192,861 to Micchelli et al., to a hairspray composition. Examples 18 and 19 were prepared having the following formulation:

| Example No. | 18 | 19 |
|---|---|---|
| AMPHOMER Resin | 3.0 | 3.0 |
| LEXAMINE L-13 | — | 0.3 |
| AMP-95 | 0.5 | 0.4 |
| Absolute Ethanol | 96.5 | 96.3 |
| | 100.0% | 100.0% |
| Knot Adhesion Test | 23.090 | 30.905 |
| Significance Level | B | A |

The compositions were prepared in the same manner as were the previous composition. The amines were dissolved in Absolute Ethanol followed by addition of the resin and the composition was stirred until a homogeneous solution was obtained. As can be seen from the results of the Knot Adhesion Test, the addition of the LEXAMINE L-13 significantly improves the adhesion of the hair spray composition. This composition can be applied from a pump spray container. The equivalent weight of the AMPHOMER Resin was stated by the manufacturer to be 2.05 milliequivalents of carboxyl radical content per gram. Thus the total neutralization of Example 18 was 86.5% by AMP-95 only and the total neutralization of Example 19 was 86.2% with 19.7% of the carboxyl radicals being neutralized by the LEXAMINE L-13.

U.S. Pat. No 4,192,861 to Micchelli suggests the use of long chain amines which preferably contain from 12 to 18 carbon atoms on a long chain alkyl radical attached to the nitrogen atom. In the following examples, the effect on adhesion of ADMA 2 which is dimethyl lauramine. The following compositions were prepared:

| Example No. | 20 | 21 | 22 |
|---|---|---|---|
| AMPHOMER Resin | 3.0 | 3.0 | 3.0 |
| ADMA 2 | — | 1.15 | 0.23 |
| AMP-95 | 0.5 | — | 0.4 |
| Absolute Etnanol | 96.5 | 95.85 | 96.37 |
| | 100.0% | 100.0% | 100.0% |

| | | | |
|---|---|---|---|
| pH (50/50)[1] | 8.16 | 8.17 | 8.32 |
| Knot Adhesion Test | 22.542 | 27.872 | 23.640 |
| Significance Level | A | A | A |
| Haze Test (50/50) | C | H | C |
| Haze Test (10/90) | C | CL | C |
| Odor | Good | Very Poor | Poor |
| Aerosol clarity (65/35)[2] | C | C | C |
| Aerosol clarity (50/50)[3] | H | C— | TR |
| Chilled Aerosol Clarity (50/50)[3] | H | C— | TR— |
| Percent Neutr.[4] | 0 | 100.0 | 20.2 |
| Total Neutr.[5] | 86.5 | 87.8 | 86.8 |

C = Clear H = Hazy CL = Cloudy TR = Trace of Haze
[1]50 Parts of hairspray composition added to 50 parts deionized water.
[2]65 Parts of hairspray composition and 35 parts isobutane.
[3]50 parts of hairspray composition and 50 parts isobutane.
[4]Percent of total carboxyl radicals neutralized, which were neutralized by ADMA 2.
[5]Percent of carboxyl radicals neutralized by all amines present.

Statistically, there was no significant difference between the Knot Adhesion Test values obtained for Examples 20–22, i.e. all had a significance level of A and were deemed to be statistically the same. Thus, the ADMA 2 did not significantly improve the adhesion of the hair spray composition while addition of LEXAMINE L-13 did statistically significantly improve the adhesion of that composition, i.e., a reading with a significance level of B is statistically significantly different from those rates "A".

Use of 100% ADMA 2 to neutralize the carboxyl radicals present in the AMPHOMER resin (Example 21) resulted in a hazy solution while Example 22 resulted in a clear solution when only small portion of ADMA 2 was employed. However, the Micchelli et al. patent teaches that at least 50% of the carboxyl radicals to be neutralized must be neutralized with the long chain amines taught in that patent. No significant level of amine odor was detectable in any of Examples 18–20 when they were sprayed into the air, other than that provided by the AMP-95. However, the presence of amine was detectable in Examples 21 and 22 which is a disadvantage to the user. Examples 20–22 were good in Aerosol Clarity and thus compatible with 35% isobutane. Examples 21–22 were reasonably compatible with 50% isobutane while Example 20 exhibited haze at a 50% level of isobutane. Thus, the use of LEXAMINE L-13 provides a significant advantage with respect to Knot Adhesion and, in this case, odor over the amines taught in the Micchelli et al. patent.

EXAMPLES 23–27

These examples show the use of LEXAMINE L-13 to improve the adhesion of hair spray compositions containing ULTRAHOLD 8 resin.

| Example No. | 23 | 24 | 25 | 26 | 27 |
|---|---|---|---|---|---|
| ULTRAHOLD 8 Resin | 2.0 | 2.0 | 2.0 | 2.0 | 2.0 |
| PVP K-90 Resin | 0.2 | 0.2 | 0.2 | 0.2 | 0.2 |
| AMP-95 | 0.2 | 0.135 | 0.135 | 0.135 | 0.135 |
| LEXAMINE L-13 | — | 0.2 | 0.2 | 0.2 | 0.2 |
| DOW CORNING Q2-5220 | 0.2 | 0.2 | 0.2 | — | — |
| SILWET L-7602 | — | — | — | 0.1 | 0.1 |
| DOW CORNING 345 | — | — | — | — | 0.1 |
| Benzyl alcohol | 0.2 | 0.2 | — | — | — |
| Absolute Ethanol | 47.15 | 47.015 | 47.215 | 47.315 | 47.215 |
| Fragrance | 0.05 | 0.05 | 0.05 | 0.05 | 0.05 |
| | 50.00% | 50.00% | 50.00% | 50.00% | 50.00% |
| Knot Adhesion Test | 17.560 | 26.790 | 27.503 | 21.457 | 15.650 |
| Significance level | C | A,B | A | C,B | C |
| Percent Neutr.[1] | 0 | 32.7 | 32.7 | 32.7 | 32.7 |
| Total Neutr.[2] | 100 | 101 | 101 | 101 | 101 |

[1]Percent of carboxyl radicals neutralized by LEXAMINE L-13
[2]Percent of carboxyl radicals neutralized by all amines present.

The ULTRAHOLD 8 resin has a manufacturer's reported acid value of 58±5 and contains about 7.5% acrylic acid which calculates as 1.06 milliequivalents of carboxyl radical content per gram. Based on the above results, it can be seen from Examples 23 and 24 that the introduction of LEXAMINE L-13 improves the Knot Adhesion value of these hairspray compositions. The "Significance Level" indicates that values obtained for the Knot Adhesion Test which have significance levels of the same letter are comparable. Thus, the knot adhesion values for Examples 24 and 25 are statistically equivalent since both have significance levels of A. The compositions having a significance of level of C are statistically significantly different from those having significance levels of A or B. The results also show that using differing types of silicones can affect the Knot Adhesion Value level.

EXAMPLES 28

In this Example, ADOGEN 185 was used in place of LEXAMINE L-13 to prepare hair spray compositions of the present invention. The formulation employed was as follows:

| Example No. | 28 |
|---|---|
| Acrylic Polymer A | 5.0 |
| DOW CORNING Q2-5220 | 0.2 |
| AMP-95 | 0.2 |
| ADOGEN 185 | 0.2 |
| Fragrance | 0.15 |
| Absolute Ethanol | 54.25 |

| Example No. | 28 |
|---|---|
| Hydrocarbon Propellant A | 40.00 |
| | 100.00% |

The composition was prepared by mixing the amines with the Absolute Ethanol until the mixture was homogeneous and thereafter adding the Acrylic Polymer A with stirring until a homogeneous solution was obtained. The silicone was then added and the mixture was stirred until a homogeneous composition was obtained. The intermediate composition (i.e., all but the propellant) was clear in appearance and was then added to a glass aerosol container and charged with the above amount of propellant. The Aerosol Clarity test was rated C- (slightly less than clear) and the Chilled Aerosol Clarity was rated as being C- with no precipitate observed. The odor of the sprayed aerosol was deemed to be good with no noticeable amine odor other than that of the aminomethyl propanol. The composition was clear, smooth and tack free when sprayed on a glass slide and allowed to dry at room temperature. The result of the 10/90 Haze Test was a slightly hazy solution. The total neutralization of carboxyl radicals was 39.4% with 25.1% of the carboxyl radicals neutralized by the LEXAMINE L-13.

EXAMPLES 29-33

In these Examples, the effect of changing the level of LEXAMINE L-13 on the adhesion values of the hair spray compositions was measured. These compositions can either be used in pump hair spray formulation or else in aerosol self-pressurized composition using 35 parts of isobutane to 65 parts of the composition below. The compositions were as follows:

| Example No. | 29 | 30 | 31 | 32 | 33 |
|---|---|---|---|---|---|
| Acrylic Polymer A | 7.5 | 7.5 | 7.5 | 7.5 | 7.5 |
| AMP-95 | 0.45 | 0.45 | 0.45 | 0.45 | 0.45 |
| LEXAMINE L-13 | 0.1 | 0.2 | 0.3 | 0.4 | 0.5 |
| Absolute Ethanol | 91.95 | 91.85 | 91.75 | 91.65 | 91.55 |
| | 100.00% | 100.00% | 100.00% | 100.00% | 100.00% |
| Knot Adhesion Test | 26.238 | 23.636 | 28.050 | 27.723 | 17.831 |
| Significance level | A | A | A | A | B |
| Percent Neutr.[1] | 6.8 | 12.7 | 17.9 | 22.6 | 26.7 |
| Total Neutr.[2] | 47.5 | 50.7 | 54.0 | 57.2 | 60.4 |
| pH (50/50)[3] | 7.55 | 7.64 | 7.66 | 7.73 | 7.81 |

[1]Percent of total carboxyl radicals neutralized which were neutralized by LEXAMINE L-13.
[2]Percent of carboxyl radicals neutralized by all amines present.
[3]50 parts of hairspray composition added to 50 parts deionized water.

All of the compositions were clear after the ingredients were homogeneously mixed and the Haze Test at 50/50 showed that all compositions remained clear. Examples 29-32 were found to be comparable in knot adhesion while Example 33 has a statistically significantly different and lower Knot Adhesion value than the other four samples. Example 33 thus appeared to have more than the optimum amount of LEXAMINE L-13 for this composition.

EXAMPLES 34-37

The following are examples of compositions which can be used in self-pressurized aerosol hairspray products (Examples 34 and 35) and in pump-spray aerosol containers (Examples 36 and 37).

| Example No. | 34 | 35 | 36 | 37 |
|---|---|---|---|---|
| Acrylic Polymer B | 2.50 | — | 6.25 | 7.50 |
| Acrylic Polymer C | 1.25 | — | — | — |
| ULTRAHOLD 8 | — | 2.00 | — | — |
| AMP-95 | 0.225 | 0.14 | 0.45 | 0.54 |
| LEXAMINE L-13 | 0.15 | 0.20 | 0.30 | 0.36 |
| SILWET L-7602 | 0.05 | — | — | — |
| DOW CORNING Q2-5220 | — | 0.20 | 0.20 | 0.20 |
| DOW CORNING 345 | 0.05 | — | — | — |
| Fragrance | 0.05 | 0.05 | 0.10 | 0.10 |
| Absolute Ethanol | 60.725 | 47.41 | 92.70 | 91.30 |
| Isobutane | 35.0 | 50.0 | — | — |
| | 100.00% | 100.00% | 100.00 | 100.00% |
| Percent Neutr.[1] | 17.9 | 31.9 | 17.9 | 21.5 |
| Total Neutr.[2] | 53.9 | 103 | 64.7 | 64.7 |

[1]Percent of total carboxyl radicals neutralized, which were neutralized by LEXAMINE L-13.
[2]Percent of carboxyl radicals neutralized by all amines present.

EXAMPLES 38-41

The following four hairspray compositions were prepared, charged in pressurized aerosol spray containers, and evaluated using a panel of 80 test subjects. The formulations used were as follows:

| Example No. | 38 | 39 | 40 | 41 |
|---|---|---|---|---|
| Acrylic Polymer A | 5.0 | 5.0 | 5.0 | 5.0 |
| ETHOMEEN 18/20 | 0.2 | 0.2 | — | — |
| AMP-95 | 0.3 | 0.3 | 0.3 | 0.3 |

-continued

| Example No. | 38 | 39 | 40 | 41 |
|---|---|---|---|---|
| LEXAMINE L-13 | — | — | 0.2 | 0.2 |
| DOW CORNING Q2-5220 | 0.2 | — | 0.2 | — |
| SILWET L-7602 | — | 0.1 | — | 0.1 |
| DOW CORNING 345 | — | 0.1 | — | 0.1 |
| Absolute Ethanol | 64.15 | 64.15 | 64.15 | 64.15 |
| Fragrance | 0.15 | 0.15 | 0.15 | 0.15 |
| Hydrocarbon Propellant A | 30.00 | 30.00 | 30.00 | 30.00 |
|  | 100.00% | 100.00% | 100.00% | 100.00% |
| Knot Adhesion Value | 12.566 | 18.865 | 26.177 | 28.107 |
| Significance Level | B | B | A | A |
| Percent Neutr.[1] | 0 | 0 | 17.9 | 17.9 |
| Total Neutr.[2] | 44.3 | 44.3 | 53.9 | 53.9 |

[1] Percent of total carboxyl radicals neutralized, which were neutralized by LEXAMINE L-13.
[2] Percent of carboxyl radicals neutralized by all amines present.

With regard to Knot Adhesion values, Examples 38 and 39 containing ETHOMEEN 18/20 were lower than the knot adhesion values observed for the LEXAMINE L-13. However, the knot adhesion value of a leading commercially available hairspray sold under the name "FINESSE" by Helene Curtis Industries, Inc. was evaluated and was found to have a knot adhesion value of 17.451 grams with a significance level of B. Thus, the compositions of Examples 38 and 39 had knot adhesion values which were comparable to that of a leading hairspray formulation, FINESSE hairspray and Examples 40–41 were better.

The purpose of the 80 member test panel was to determine what effects the amines and the silicones might have on the perceived performance of the hairspray compositions. The conclusion of the study was that parity performance was seen between the amines, with the exception that the LEXAMINE L-13 compositions were judged to have more resistance to blowing by the wind and a softer and less sticky feel than the compositions containing ETHOMEEN 18/20. The compositions containing the DOW CORNING Q2-5220 as a modifier were observed to have more beading, a less wet spray, were stickier and had less body 6 to 8 hours later than did the compositions containing SILWET L-7602 and DOW CORNING 345 Fluid. Thus, Example 41 appeared to have the most desirable properties for a hairspray compositions based on the 80 person panel test of these four formulations.

That which is claimed is:

1. A hair setting composition having improved adhesion to the hair and removability from the hair upon washing comprising from 0.5% to 8% by weight of a hair setting resin containing pendant carboxyl radicals and a solvent for the resin wherein from about 10 to 100% of the carboxyl radicals are neutralized with a neutralizing agent consisting of
   (a) up to 40 mole percent, based on the mole percent of the carboxyl radicals to be neutralized, of at least one long chain amine selected from the group consisting of $R^1CONHR^2NR^3R^4$ where $R^1$ is a hydrocarbon radical having from about 9 to 14 carbon atoms, $R^2$ is an alkylene radical of 2 to 4 carbon atoms, and each of $R^3$ and $R^4$ are alkyl radicals of 1 to 2 carbon atoms or hydrogen, $$R^5N\begin{matrix}(CH_2CH_2O)_xH \\ (CH_2CH_2O)_yH\end{matrix}$$

where $R^5$ is a hydrocarbon radical having from 10 to 18 carbon atoms and the sum of $x+y$ has an average value of from about 5 to 25, and $R^6OR^7NR^8R^9$ where $R^6$ is a hydrocarbon radical of from 8 to 16 carbon atoms, $R^7$ is an alkyl radical of 1 to 2 carbon atoms, and each of $R^8$ and $R^9$ are alkyl radicals of 1 to 2 carbon atoms or hydrogen; and
   (b) the balance of the neutralizing agent being a water soluble, cosmetically acceptable basic compound, said hair setting resin being a polymer of an acid selected from the group consisting of acrylic acid, methacrylic acid, crotonic acid and maleic anhydride and at least one monomer selected from the group consisting of monoesters and amides of an acid selected from the group consisting of acrylic acid and methacrylic acid, vinyl acetate and methyl vinyl ether.
   (b) the balance of the neutralizing agent being a water soluble, cosmetically acceptable basic compound.

2. The composition as claimed in claim 1 wherein the amount of long chain amine is in the range of from 5% to 30% of the carboxyl radicals to be neutralized.

3. The composition as claimed in claim 1 wherein the long chain amine is selected from the group consisting of a long chain amido amine wherein $R^1$ is a $C_{11}$ alkyl radical, $R^2$ is $-(CH_2)_3-$ and $R^3$ and $R^4$ are each methyl radicals, an N-ethoxylated amine wherein $R^5$ is a $C_{18}$ alkyl radical and the sum of $x+y$ has an average value of about 10, and a mixture of ether amines wherein $R^6$ is predominantly composed of $C_{12}$ to $C_{15}$ hydrocarbon radicals, $R^7$ is $-(CH_2)_3-$ and $R^8$ and $R^9$ are each hydrogen atoms.

4. The composition as claimed in claim 1 wherein the long chain amine is along chain amido amine wherein $R^1$ is a $C_{11}$ alkyl radical, $R^2$ is $-(CH_2)_3-$ and $R^3$ and $R^4$ are each methyl radicals.

5. The composition as claimed in claim 1 wherein the balance of the neutralizing agent is selected from the group consisting of an amine or alkanolamine selected from the group consisting of ammonia, ammonium hydroxide, monoethanolamine, diethanolamine, triethanolamine, monopropanolamine, dipropanolamine, tripropanolamine, morpholine, aminoethyl ethanolamine, aminomethyl propanol, aminomethyl propanediol, 4-morpholineethanol, ammonium salts of lysine or glycine and mixtures thereof.

6. The composition as claimed in claim 1 wherein the solvent for said resin is selected from the group consisting of $C_2$ to $C_4$ alcohols, water and mixtures thereof.

7. The composition as claimed in claim 1 wherein the solvent is selected from the group consisting of water, ethanol and isopropanol.

8. The composition as claimed in claim 1 wherein the solvent is water and the composition further contains a thickener.

9. The composition as claimed in claim 8 wherein the thickener is selected from the group consisting of at least one water soluble cellulosic polymer or an acrylic acid homopolymer crosslinked with a small amount of a polyallyl ether of sucrose.

10. The composition of claim 1 wherein the resin is a polymer wherein the carboxyl radicals are derived from acrylic acid or methacrylic acid and the remainder of the polymer is derived from at least one monomer selected from the group consisting of esters of acrylic acid or methacrylic acid with $C_1$ to $C_{18}$ alcohols, hydroxymonoesters of acrylic acid or methacrylic acid with $C_2$ to $C_6$ glycols, hydroxymonoesters of acrylic acid or methacrylic acid with polyalkyleneoxy polymers containing up to about 25 units derived from the group consisting of ethylene oxide, propylene oxide and mixtures thereof, acrylamide, methacrlyamide, and N-substituted acrylamides or methacrylamides substituted with alkyl radicals having from 2 to 12 carbon atoms.

11. The composition of claim 1 wherein the resin is selected from the group consisting of a polymer of tertiary-butyl acrylamide, acrylic acid and ethylacrylate; a polymer of N-tert-octyl acrylamide, methyl methacrylate, 2-hydroxypropyl methacrylate, acrylic acid and t-butyl aminoethyl methacrylate; and a polymer of methacrylic acid, butyl acrylate and ethyl methacrylate.

12. The composition of claim 1 which further contains from 10% to about 80% of an aerosol propellant.

13. A hairspray composition having improved hydrocarbon propellant compatibility, adhesion to the hair and removability from the hair upon washing comprising from 0.5% to 6% by weight of a hairspray resin containing pendant carboxyl radicals, from 10% to 80% of a volatile hydrocarbon propellant, and a solvent for the resin wherein from about 10% to 100% of the carboxyl radicals are neutralized with a neutralizing agent consisting of (a) up to 40 mole percent, based on the mole percent of the carboxyl radicals to be neutralized, of at least one long chain amine selected from the group consisting of

where $R^1$ is a hydrocarbon radical having from about 9 to 14 carbon atoms, $R^2$ is an alkylene radical of 2 to 4 carbon atoms, and each of $R^3$ and $R^4$ are alkyl radicals of 1 to 2 carbon atoms or hydrogen,

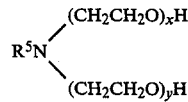

where $R^5$ is a hydrocarbon radical having from 10 to 18 carbon atoms and the sum of $x+y$ has an average value of from about 5 to 25, and

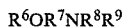

where $R^6$ is a hydrocarbon radical of from 8 to 16 carbon atoms, $R^7$ is an alkyl radical of 1 to 2 carbon atoms, and each of $R^8$ and $R^9$ are alkyl radicals of 1 to 2 carbon atoms or hydrogen; and (b) the balance of the neutralizing agent being a water soluble, cosmetically acceptable basic compound, said hair setting resin being a polymer of an acid selected from the group consisting of acrylic acid, methacrylic acid, crotonic acid and maleic anhydride and at least one monomer selected from the group consisting of monoesters and amides of an acid selected from the group consisting of acrylic acid and methacrylic acid, vinyl acetate and methyl vinyl ether.

14. The composition as claimed in claim 13 wherein the amount of long chain amine is in the range of from 5% to 30% of the carboxyl radicals to be neutralized.

15. The composition as claimed in claim 13 wherein the long chain amine is selected from the group consisting of a long chain amido amine wherein $R^1$ is a $C_{11}$ alkyl radial, $R^2$ is —$(CH_2)_3$— and $R^3$ and $R^4$ are each methyl radicals, an N-ethoxylated amine wherein $R^5$ is a $C_{18}$ alkyl radical and the sum of $x+y$ has an average value of about 10, and a mixture of ether amines wherein $R^6$ is predominantly composed of $C_{12}$ to $C_{15}$ hydrocarbon radicals, $R^7$ is —$(CH_2)_3$— and $R^8$ and $R^9$ are each hydrogen atoms.

16. The composition as claimed in claim 13 wherein the long chain amine is a long chain amido amine wherein $R^1$ is a $C_{11}$ alkyl radical, $R^2$ is —$(CH_2)_3$— and $R^3$ and $R^4$ are each methyl radicals.

17. The composition as claimed in claim 13 wherein the balance of the neutralizing agent is selected from the group consisting of an amine or alkanolamine selected from the group consisting of ammonia, ammonium hydroxide, monoethanolamine, diethanolamine, triethanolamine, monopropanolamine, dipropanolamine, tripropanolamine, morpholine, aminoethyl ethanolamine, aminomethyl propanol, aminomethyl propanediol, 4-morpholineethanol, ammonium salts of lysine or glycine and mixtures thereof.

18. The composition as claimed in claim 13 wherein the solvent for said resin is selected from the group consisting of $C_2$ to $C_4$ alcohols, water and mixtures thereof.

19. The composition as claimed in claim 13 wherein the solvent is not more than about 10% water and the balance of the solvent is selected from the group consisting of ethanol and isopropanol.

20. The composition as claimed in claim 13 wherein propellant is from 20 to 50% of the composition.

21. The composition as claimed in claim 13 wherein the propellant is selected from the group consisting of butane, isobutane, propane and mixtures.

22. The composition of claim 13 wherein the resin is a polymer wherein the carboxyl radicals are derived from acrylic acid or methacrylic acid and the remainder of the polymer is derived from at least one monomer selected from the group consisting of esters of acrylic acid or methacrylic acid with $C_1$ to $C_{18}$ alcohols, hydroxymonoesters of acrylic acid or methacrylic acid with $C_2$ to $C_6$ glycols, hydroxymonoesters of acrylic acid or methacrylic acid with polyalkyleneoxy polymers containing up to about 25 units derived from the group consisting of ethylene oxide, propylene oxide and mixtures thereof, acrylamide, methacrylamide, and N-substituted acrylamides or methacrylamides substituted with alkyl radicals having from 2 to 12 carbon atoms.

23. The composition of claim 13 wherein the resin is selected from the group consisting of a polymer of tertiary-butyl acrylamide, acrylic acid and ethylacrylate; a polymer of N-tert-octyl acrylamide, methyl methacrylate, 2-hydroxypropyl methacrylate, acrylic acid and t-butyl aminoethyl methacrylate; and a polymer of methacrylic acid, butyl acrylate and ethyl methacrylate.

* * * * *

UNITED STATES PATENT AND TRADEMARK OFFICE
CERTIFICATE OF CORRECTION

PATENT NO. : 4,874,604
DATED : October 17, 1989
INVENTOR(S) : John A. Sramek

It is certified that error appears in the above-identified patent and that said Letters Patent is hereby corrected as shown below:

In column 3, line 68, "hydrogen." should be --hydrogen,--.

In column 4, line 8, "X + y" should be --x + y--.

In column 4, line 16, the word "of" should be --or--.

In column 20, lines 43-44, the phrase "(b) the balance of the neutralizing agent being a water soluble, cosmetically acceptable basic compound." should be deleted.

In column 20, line 59, the word "along" should be --a long--.

In column 21, line 29, the word "methacrlyamide" should be --methacrylamide--.

Signed and Sealed this

Eighth Day of October, 1991

Attest:

HARRY F. MANBECK, JR.

*Attesting Officer*  *Commissioner of Patents and Trademarks*